(12) United States Patent
Gono (10) Patent No.: US 8,216,126 B2
(45) Date of Patent: Jul. 10, 2012

(54) LIVING BODY OBSERVING APPARATUS (75) Inventor: Kazuhiro Gono, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 1237 days.

(21) Appl. No.: 11/993,123

(22) PCT Filed: Jun. 22, 2006

(86) PCT No.: PCT/JP2006/312527
§ 371 (c)(1),
(2), (4) Date: Dec. 19, 2007

(87) PCT Pub. No.: WO2007/013245
PCT Pub. Date: Feb. 1, 2007

(65) Prior Publication Data
US 2010/0217077 A1     Aug. 26, 2010

(30) Foreign Application Priority Data
Jul. 28, 2005   (JP) .................. 2005-219468

(51) Int. Cl.
  *A61B 1/06*   (2006.01)
  *A61B 1/04*   (2006.01)
(52) U.S. Cl. ................. 600/109; 600/178; 600/179
(58) Field of Classification Search .......... 600/109, 600/324, 339, 180, 178, 173, 118, 477, 182, 600/181, 179; 606/109
See application file for complete search history.

(56) References Cited

U.S. PATENT DOCUMENTS
4,934,339 A   6/1990  Kato
5,078,150 A * 1/1992  Hara et al. ............ 600/476
5,515,449 A   5/1996  Tsuruoka et al.
(Continued)

FOREIGN PATENT DOCUMENTS
| EP | 1 258 220 | | 11/2002 |
| EP | 1 258 221 | A2 | 11/2002 |
| EP | 1 488 731 | A1 | 12/2004 |

(Continued)

OTHER PUBLICATIONS
Chinese Office Action dated Oct. 30, 2009.

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

There is provided a living body observing apparatus capable of reducing time period to be spent on observation of a subject in a living body. The living body observing apparatus of the invention includes: illumination means including one or a plurality of semiconductor light emitting elements for emitting illumination light to illuminate a subject; image pickup means for picking up an image of the subject illuminated by the illumination light emitted from the illumination means, and outputting the picked-up image as an image pickup signal; color separation means for separating the image of the subject into red, green, and blue components; and image processing means for performing a predetermined processing on the image pickup signal outputted from the image pickup means, and outputting the processed image pickup signal as a video signal to display the image of the subject on display means. The image processing means performs, as the predetermined processing, color conversion processing to convert the blue component in the image pickup signal into a green component in the video signal, and convert the green component in the image pickup signal into a red component in the video signal.

15 Claims, 4 Drawing Sheets

U.S. PATENT DOCUMENTS

| | | |
|---|---|---|
| 6,422,994 B1 * | 7/2002 | Kaneko et al. ............... 600/160 |
| 2002/0062061 A1 * | 5/2002 | Kaneko et al. ............... 600/118 |
| 2002/0177751 A1 | 11/2002 | Ueno et al. |
| 2003/0139650 A1 * | 7/2003 | Homma ........................ 600/181 |
| 2003/0176768 A1 * | 9/2003 | Gono et al. .................. 600/109 |
| 2004/0046865 A1 | 3/2004 | Ueno et al. |
| 2005/0245789 A1 * | 11/2005 | Smith et al. .................. 600/159 |
| 2006/0173358 A1 * | 8/2006 | Xie ............................... 600/476 |

FOREIGN PATENT DOCUMENTS

| | | |
|---|---|---|
| JP | 04-075627 | 3/1992 |
| JP | 10-325798 | 12/1998 |
| JP | 2002-238846 | 8/2002 |
| JP | 2003-102680 | 4/2003 |
| JP | 2006-218283 | 8/2006 |
| TW | I222833 | 10/2004 |

* cited by examiner

LIVING BODY OBSERVING APPARATUS

TECHNICAL FIELD

The present invention relates to a living body observing apparatus, and more particularly to a living body observing apparatus capable of picking up an image of blood vessels and the like on a mucosa surface layer in a living body with high contrast.

BACKGROUND ART

Conventionally, an endoscope apparatus including an endoscope, a light source device, and the like has been widely used in a medical field and the like. The endoscope apparatus in the medical field, in particular, is mainly used for the purpose of observation and the like in a living body as a subject to be inspected by an operator or the like. As the light source device used in the above-described endoscope apparatus, there is proposed a light source device for endoscope in Japanese Unexamined Patent Application Publication No. 2002-238846, for example.

In addition, commonly known observation by using the endoscope apparatus in the medical field includes, for example, in addition to normal observation in which a subject in a living body is irradiated with white light to pick up an image of the subject generally the same as that in observation with the naked eye, narrow band observation (NBI: Narrow Band Imaging) in which an image of blood vessels and the like on a mucosa surface layer in a living body can be picked up with high contrast compared with the normal observation, by performing observation irradiating a subject with narrow-band light having a narrower wavelength band than illumination light in the normal observation.

A light source device for endoscope proposed in Japanese Unexamined Patent Application Publication No. 2002-238846 includes three LEDs, that is, R (red), G (green), and B (blue) LEDs, an LED control circuit for controlling light emission intensity of each of the three LEDs, and a color adjustment switch capable of adjusting the light emission intensity of each of the three LEDs, through the LED control circuit, by an operation by an operator or the like. With the above-described configuration, the light source device for endoscope proposed in Japanese Unexamined Patent Application Publication No. 2002-238846 is capable of freely adjusting the color of an image of a subject in a living body picked up by the endoscope, as needed.

However, the light source device for endoscope proposed in Japanese Unexamined Patent Application Publication No. 2002-238846 does not include color adjustment means for adjusting the color of the subject image which supports narrow band observation. Therefore, in the observation using the light source device for endoscope proposed in Japanese Unexamined Patent Application Publication No. 2002-238846, an operator or the like is required to perform narrow band observation using a dedicated device such as another light source device and the like, for example. As a result, there is a problem that the time period to be spent on the observation of a subject in a living body becomes longer.

The present invention has been achieved in view of the above-described circumstances, and the object of the present invention is to provide a living body observing apparatus capable of reducing the time period to be spent on observation of a subject in a living body.

DISCLOSURE OF INVENTION

Means for Solving the Problem

A living body observing apparatus of a first aspect of the present invention comprises: illumination means including one or a plurality of semiconductor light emitting elements for emitting illumination light to illuminate a subject; image pickup means for picking up an image of the subject illuminated by the illumination light emitted from the illumination means, and outputting the picked-up image as an image pickup signal; color separation means for separating the image of the subject into red, green, and blue components; and image processing means for performing a predetermined processing on the image pickup signal outputted from the image pickup means, and outputting the processed image pickup signal as a video signal to display the image of the subject on display means, wherein the image processing means performs, as the predetermined processing, color conversion processing to convert the blue component in the image pickup signal into a green component in the video signal, and convert the green component in the image pickup signal into a red component in the video signal.

A living body observing apparatus of a second aspect of the present invention comprises: illumination means including one or a plurality of semiconductor light emitting elements for emitting illumination light to illuminate a subject; image pickup means for picking up an image of the subject illuminated by the illumination light emitted from the illumination means, and outputting the picked-up image as an image pickup signal; color separation means for separating the image of the subject into red, green, and blue components; and image processing means for performing a predetermined processing on the image pickup signal outputted from the image pickup means, and outputting the processed image pickup signal as a video signal to display the image of the subject on display means, wherein the image processing means performs, as the predetermined processing, color conversion processing to convert the blue component in the image pickup signal into a green component and a blue component in the video signal, and convert the green component in the image pickup signal into a red component in the video signal.

A living body observing apparatus of a third aspect of the present invention is the living body observing apparatus of the first aspect, wherein the illumination means includes a fluorescent member for emitting fluorescence as the illumination light excited by excitation light including a predetermined wavelength band and the semiconductor light emitting element emits the excitation light to the fluorescent member.

A living body observing apparatus of a fourth aspect of the present invention is the living body observing apparatus of the second aspect, wherein the illumination means includes a fluorescent member for emitting fluorescence as the illumination light excited by excitation light including a predetermined wavelength band, and the semiconductor light emitting element emits the excitation light to the fluorescent member.

A living body observing apparatus of a fifth aspect of the present invention is the living body observing apparatus of the first aspect, wherein the color separation means is provided on a pathway from the subject to the image pickup means.

A living body observing apparatus of a sixth aspect of the present invention is the living body observing apparatus of the second aspect, wherein the color separation means is provided on a pathway from the subject to the image pickup means.

A living body observing apparatus of a seventh aspect of the present invention is the living body observing apparatus of the first aspect, wherein the illumination means, the image pickup means, and the color separation means are provided inside of an endoscope.

A living body observing apparatus of a eighth aspect of the present invention is the living body observing apparatus of the second aspect, wherein the illumination means, the image pickup means, and the color separation means are provided inside of an endoscope.

A living body observing apparatus of a ninth aspect of the present invention is the living body observing apparatus of the first aspect, wherein the illumination means, the image pickup means, and the color separation means are provided inside of an oral camera.

A living body observing apparatus of a tenth aspect of the present invention is the living body observing apparatus of the second aspect, wherein the illumination means, the image pickup means, and the color separation means are provided inside of an oral camera.

A living body observing apparatus of an eleventh aspect of the present invention is the living body observing apparatus of the third aspect, wherein the predetermined wavelength band is in blue range.

A living body observing apparatus of a twelfth aspect of the present invention is the living body observing apparatus of the fourth aspect, wherein the predetermined wavelength band is in blue range.

A living body observing apparatus of a thirteenth aspect of the present invention is the living body observing apparatus of the third aspect, wherein the fluorescence is light including blue or green wavelength band.

A living body observing apparatus of a fourteenth aspect of the present invention is the living body observing apparatus of the fourth aspect, wherein the fluorescence is light including blue or green wavelength band.

A living body observing apparatus of a fifteenth aspect of the present invention is the living body observing apparatus of the eleventh aspect, wherein the fluorescence is light including blue or green wavelength band.

A living body observing apparatus of a sixteenth aspect of the present invention is the living body observing apparatus of the twelfth aspect, wherein the fluorescence is light including blue or green wavelength band.

A living body observing apparatus of a seventeenth aspect of the present invention comprises: illumination means including a plurality of semiconductor light emitting elements for respectively emitting lights including different color wavelength bands as illumination lights to illuminate a subject; image pickup means for picking up an image of the subject illuminated by the illumination lights emitted from the illumination means, and outputting the picked-up image as an image pickup signal; color separation means for separating the image of the subject into red, green, and blue components; and image processing means for performing a predetermined processing on the image pickup signal outputted from the image pickup means, outputting the processed image pickup signal as a video signal to display the image of the subject on display means, wherein the image processing means performs, as the predetermined processing, color conversion processing to convert the blue component in the image pickup signal into a green component in the video signal, and convert the green component in the image pickup signal into a red component in the video signal.

A living body observing apparatus of a eighteenth aspect of the present invention is the living body observing apparatus of the seventeenth aspect, wherein the color separation means is provided in the illumination means.

BEST MODE FOR CARRYING OUT THE INVENTION

Hereinafter, embodiments of the present invention are described with reference to the drawings.
(First Embodiment)

Figure 1:
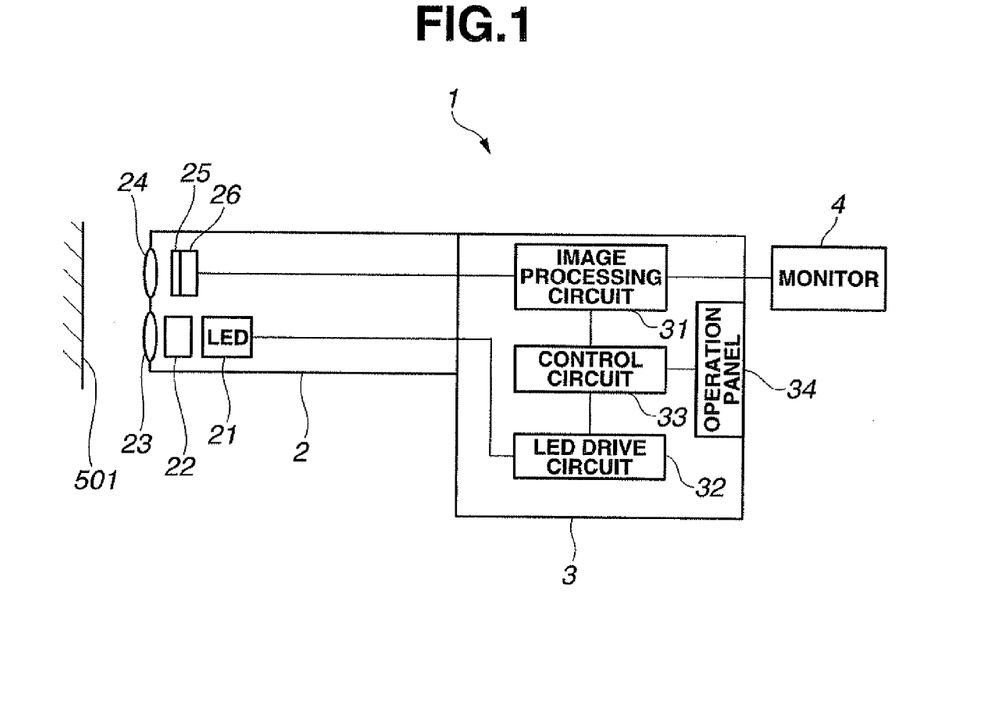
FIG. 1 is a view showing an exemplary configuration of a main part of a living body observing apparatus according to a first embodiment.
Figure 2:
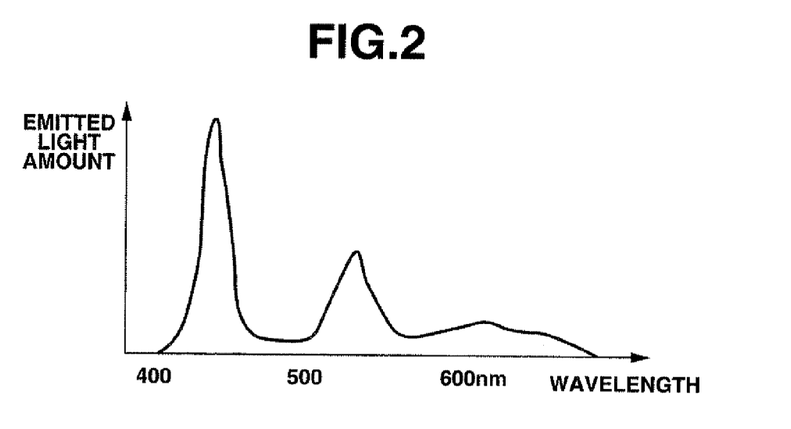
FIG. 2 is a view showing an exemplary correlation between a wavelength band and an emitted light amount of narrow-band light emitted from a living body image pickup device according to the first embodiment.
Figure 3:
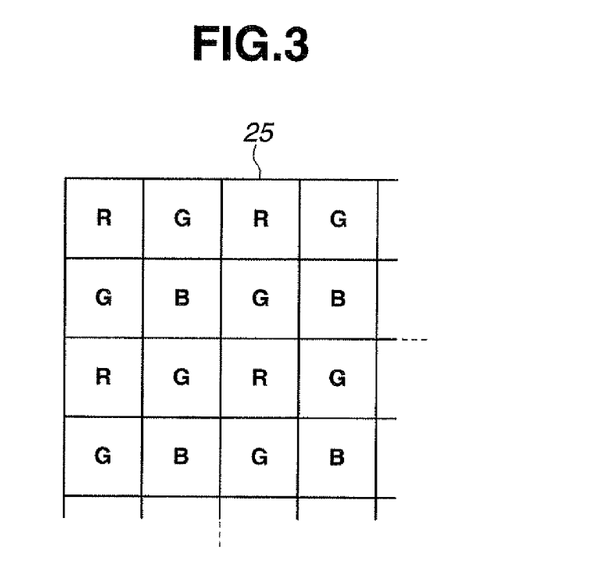
FIG. 3 is a view showing an exemplary configuration of a color filter included in the living body image pickup device according to the first embodiment.
Figure 4:
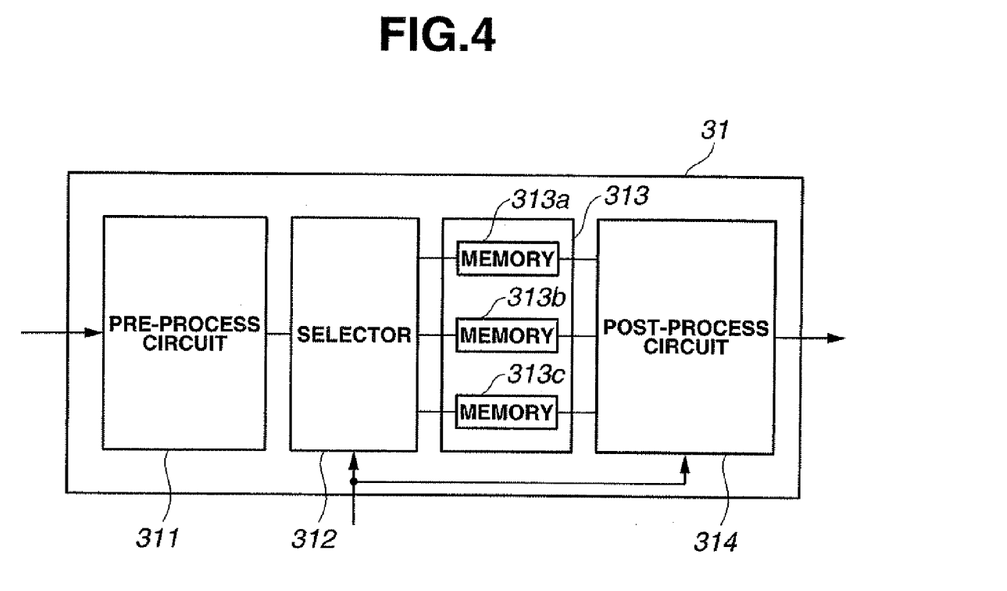
FIG. 4 is a view showing an exemplary configuration of an image processing circuit included in an image processing device according to the first embodiment.
Figure 5:
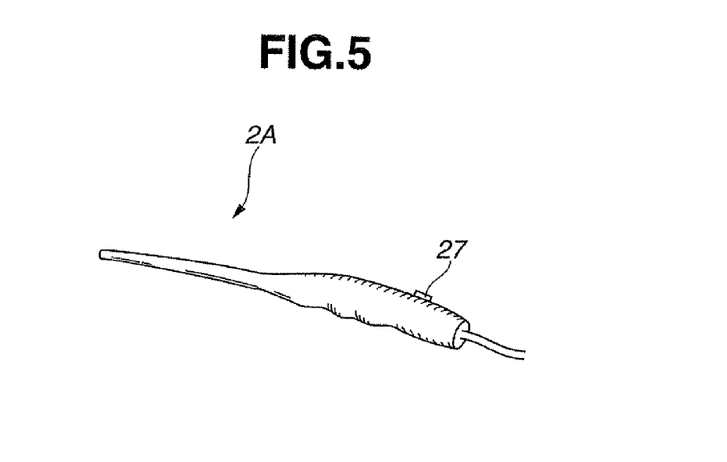
FIG. 5 is a view showing an exemplary appearance of an oral camera used as the living body image pickup device configuring the living body observing apparatus according to the first embodiment.

FIGS. 1 to 5 relate to a first embodiment of the present invention. FIG. 1 is a view showing an exemplary configuration of a main part of a living body observing apparatus according to the present embodiment. FIG. 2 is a view showing an exemplary correlation between a wavelength band and an emitted light amount of narrow-band light emitted from a living body image pickup device according to the present embodiment. FIG. 3 is a view showing an exemplary configuration of a color filter included in the living body image pickup device according to the present embodiment. FIG. 4 is a view showing an exemplary configuration of an image processing circuit included in an image processing device according to the present embodiment. FIG. 5 is a view showing an exemplary appearance of an oral camera used as the living body image pickup device configuring the living body observing apparatus according to the present embodiment.

As shown in FIG. 1, a living body observing apparatus 1 includes, as a main part: a living body image pickup device 2, for example an endoscope, for picking up an image of a subject 501 such as living tissue and the like in a living body as a subject to be inspected, to output the picked-up image as an image pickup signal; an image processing device 3 for generating a video signal based on the image pickup signal outputted from the living body image pickup device 2 to output the generated video signal; and a monitor 4, as display means, for displaying an image of the subject 501 picked up by the living body image pickup device 2, based on the video signal outputted from the image processing device 3.

The living body image pickup device 2 includes an LED 21, a fluorescent member 22 configured of white paint and the like, for example, which emits fluorescence excited by excitation light emitted from the LED 21, an illumination optical system 23, an objective optical system 24, a color filter 25, and a CCD (charge coupled device) 26.

The LED 21 configuring a part of illumination means in the living body observing apparatus 1 emits light based on a driving voltage supplied from the image processing device 3 to emit light including blue wavelength band as excitation light for exciting the fluorescent member 22 configuring a part of the illumination means in the living body observing apparatus 1.

The fluorescence radiated from the fluorescent member 22 as a result of excitation by the excitation light emitted from the LED 21 is emitted to the subject 501 via the illumination optical system 23 as narrow-band light having peaks in the blue and green wavelength bands shown in FIG. 2, for example.

The objective optical system 24 fowls an image of the subject 501 illuminated by the narrow-band light emitted from the illumination optical system 23.

The color filter 25 as color separation means in the living body observing apparatus 1 is provided on an image pickup surface of a CCD 26, and has a configuration in which, for example, each of R, G, B color filters provided corresponding to each pixel is arranged in a matrix pattern as shown in FIG. 3. With the above-described configuration, the color filter 25 performs color separation on the image of the subject 501 formed by the objective optical system 24.

The CCD 26 as image pickup means picks up the image of the subject 501 which has been subjected to color separation by the color filter 25, to output the picked-up image of the subject 501 as an image pickup signal to the image processing device 3.

The image processing device 3 as image processing means in the living body observing apparatus 1 includes an image processing circuit 31, an LED drive circuit 32, a control circuit 33, and an operation panel 34.

As shown in FIG. 4, the image processing circuit 31 includes a pre-process circuit 311, a selector 312, a synchronizing circuit 313, and a post-process circuit 314.

The pre-process circuit 311 performs processings such as amplification, A/D conversion, and correlated double sampling on the image pickup signal outputted from the CCD 26, and thereafter outputs the image pickup signal subjected to the processings to the selector 312.

The selector 312 outputs, based on the control signal outputted from the control circuit 33, an R component, a G component, and a B component, as each of the color components in the image pickup signal outputted from the pre-process circuit 311, to the synchronizing circuit 313.

The synchronizing circuit 313 includes memories 313a, 313b, and 313c. The synchronizing circuit 313 stores each of the color components in the image pickup signal outputted from the selector 312 in the memories 313a, 313b, and 313c, respectively, and thereafter synchronously outputs the color components to the post-process circuit 314.

The post-process circuit 314 performs, based on the control signal outputted from the control circuit 33, processings such as color conversion, γ correction, and D/A conversion on the image pickup signal outputted from the synchronizing circuit 313. Then, the post-process circuit 314, by performing the above-described processings, converts the image pickup signal into a video signal and outputs the video signal to the monitor 4.

Based on the control signal outputted from the control circuit 33, the LED drive circuit 32 supplies a driving voltage to cause the LED 21 to emit light.

The control circuit 33 such as a CPU (central processing unit) outputs control signals to the selector 312 and the post-process circuit 314 in the image processing circuit 31, and the LED drive circuit 32 to cause the selector 312, the post-process circuit 314, and the LED drive circuit 32 to respectively perform processings according to the observation mode, based on an observation mode changeover signal outputted through the operation panel 34.

The operation panel 34 includes an observation mode changeover switch and the like for outputting an observation mode changeover signal to give instruction for changing over the observation mode in the living body image pickup device 2 and the image processing device 3 by an operation by an operator or the like, for example.

Next, description is made on working of the living body observing apparatus 1 according to the present embodiment.

An operator or the like turns on a power source of each of the devices of the living body observing apparatus 1, that is, the living body image pickup device 2, the image processing device 3, and the monitor 4 to bring each of the devices into an activation state. Note that in the above-described activation state, it is assumed that the living body image pickup device 2 and the image processing device 3 are set in a normal observation mode.

After that, the operator or the like operates and moves the living body image pickup device 2 such that a desired subject in a living body is located in a position within a field of view of the objective optical system 24, which is illuminated by narrow-band light emitted from the illumination optical system 23.

The image of the subject 501 illuminated by the narrow-band light emitted from the illumination optical system 23 in the state as described above is formed by the objective optical system 24, subjected to color separation by the color filter 25, and picked up by the CCD 26, and thereafter outputted to the image processing circuit 31 of the image processing device 3 as an image pickup signal.

The image pickup signal outputted from the CCD 26 to the image processing circuit 31 is subjected to processings such as amplification, A/D conversion, and correlated double sampling in the pre-process circuit 311, then, via the selector 312, subjected to synchronization in the synchronizing circuit 313, and thereafter inputted to the post-process circuit 314.

The post-process circuit 314 performs, based on the control signal outputted from the control circuit 33, processings such as color conversion, γ correction, and D/A conversion in the normal observation mode on the image pickup signal outputted from the synchronizing circuit 313 so as to achieve natural color reproduction generally the same as that in a state where the subject is observed with the naked eye, for example, and then outputs the image pickup signal subjected to the processings to the monitor 4 as a video signal.

As a result that the above-described controls and processings are performed in the living body image pickup device 2 and the image processing device 3, on the monitor 4 is displayed the image of a desired subject in a living body generally the same as one in a case where the subject is observed with the naked eye, as a subject image in the normal observation mode based on the video signal outputted from the image processing device 3.

When an instruction is given to change over the observation mode in the living body image pickup device 2 and the image processing device 3 for example from the normal observation mode to the narrow band observation mode by an operation of the observation mode changeover switch provided on the operation panel 34 by an operator or the like, the observation mode changeover signal based on the instruction is outputted to the control circuit 33 through the operation panel 34.

The control circuit 33 outputs control signals to the selector 312 and the post-process circuit 314 in the image processing circuit 31, and the LED drive circuit 32 to cause the selector 312, the post-process circuit 314 and the LED drive circuit 32 to respectively perform processings according to the observation mode, based on the observation mode changeover signal outputted through the operation panel 34.

Based on the control signal outputted from the control circuit 33, the selector 312 in the image processing circuit 31 outputs the G component in the image pickup signal outputted from the pre-process circuit 311 to one of the memories 313a, 313b, and 313c included in the synchronizing circuit 313, and outputs the B component in the image pickup signal outputted from the pre-process circuit 311 to the two memories other than the above-described one memory out of the memories 313a, 313b, and 313c included in the synchronizing circuit 313. Note that, it is assumed that, in the narrow band observation mode according to the present embodiment, the R component in the image pickup signal outputted from the pre-process circuit 311 is cut off by the selector 312 and the R component is not used in the subsequent processings.

The image pickup signal having two B components and one G component which is outputted from the selector 312 as a result of the above-described processing is subjected to synchronization in the synchronizing circuit 313 to be inputted to the post-process circuit 314.

The post-process circuit 314 performs, based on the control signal outputted from the control circuit 33, processings such as color conversion, γ correction, and D/A conversion in the narrow band observation mode on the image pickup signal outputted from the synchronizing circuit 313 so as to achieve color reproduction of the blood vessels, the minute structure and the like of the mucosa surface layer of the subject in the living body with high contrast, for example, and thereafter outputs the image pickup signal subjected to the processings to the monitor 4 as a video signal.

More particularly, the post-process circuit 314 performs, as the above-described color conversion processing in the narrow band observation mode, for example, processings so as to multiply one of the two B components in the image pickup signal outputted from the synchronizing circuit 313 by a weighting factor k1, the other of the two B components by a weighting factor k2, and the G component by a weighting factor k3. After performing the color conversion processing of the above-described content, the post-process circuit 314 further performs, based on a B channel signal composed of B component multiplied by the weighting factor k1, a G channel signal composed of B component multiplied by the weighting factor k2, and an R channel signal composed of G component multiplied by the weighting factor k3, processings such as γ correction and D/A conversion on the signal obtained by composing each of the channel signals to generate a video signal, and thereafter outputs the generated video signal to the monitor 4.

Note that it is assumed that the weighting factors k1, k2, and k3 used in the color conversion processing of the above-described content are real numbers. The weighting factors k1, k2, and k3, for example, may be respectively set to desired values by an operator or the like by operation of the operation panel 34, or may be fixed values set in advance in the post-process circuit 314. Furthermore, the weighting factors k1, k2, and k3 may be respectively different values, or any two of the factors or all the factors may be the same.

As a result that the above-described controls and processings are performed in the living body image pickup device 2 and the image processing device 3, on the monitor 4 is displayed an image in which the colors of the blood vessels, the minute structure and the like of the mucosa surface layer of the subject in the living body are reproduced with high contrast, as a subject image in the narrow band observation mode based on the video signal outputted from the image processing device 3.

Note that the living body image pickup device 2 as an endoscope configured to realize the above-described working may be configured, in addition to the above-described configuration, as an oral camera 2A as shown in FIG. 5, for example, having on outer surface thereof an observation mode changeover switch 27 through which an observation mode changeover signal generally the same as one outputted through the operation panel 34 is outputted to the control circuit 33 of the image processing device 3 when operated by an operator or the like.

When observation in the narrow band observation mode is performed in a state where the oral camera 2A is used instead of the living body image pickup device 2, on the monitor 4 is displayed an image in which the colors of the region in the oral cavity in the living body where plaque, tooth decay, and gingival inflammation exist are reproduced with high contrast, as a subject image in the narrow band observation mode.

Note that, as for the subject images in the normal observation mode and the narrow band observation mode which are displayed on the monitor 4 based on the video signal outputted from the image processing device 3, only either one of the images may be displayed in accordance with the changeover of the observation mode, or both of the images may be displayed separately on the monitor 4.

As described above, the living body observing apparatus 1 of the present embodiment is capable of adjusting the color of the subject image in the two kinds of observation modes, that is, the normal observation mode and the narrow band observation mode, depending on each of the observation modes. Therefore, in the observation using the living body observing apparatus 1, the operator or the like can perform the narrow band observation without using a dedicated device such as another light source device, for example. As a result, the time period to be spent on the observation of the subject in a living body can be reduced compared with the observation using a conventional apparatus.

(Second Embodiment)

Figure 6:
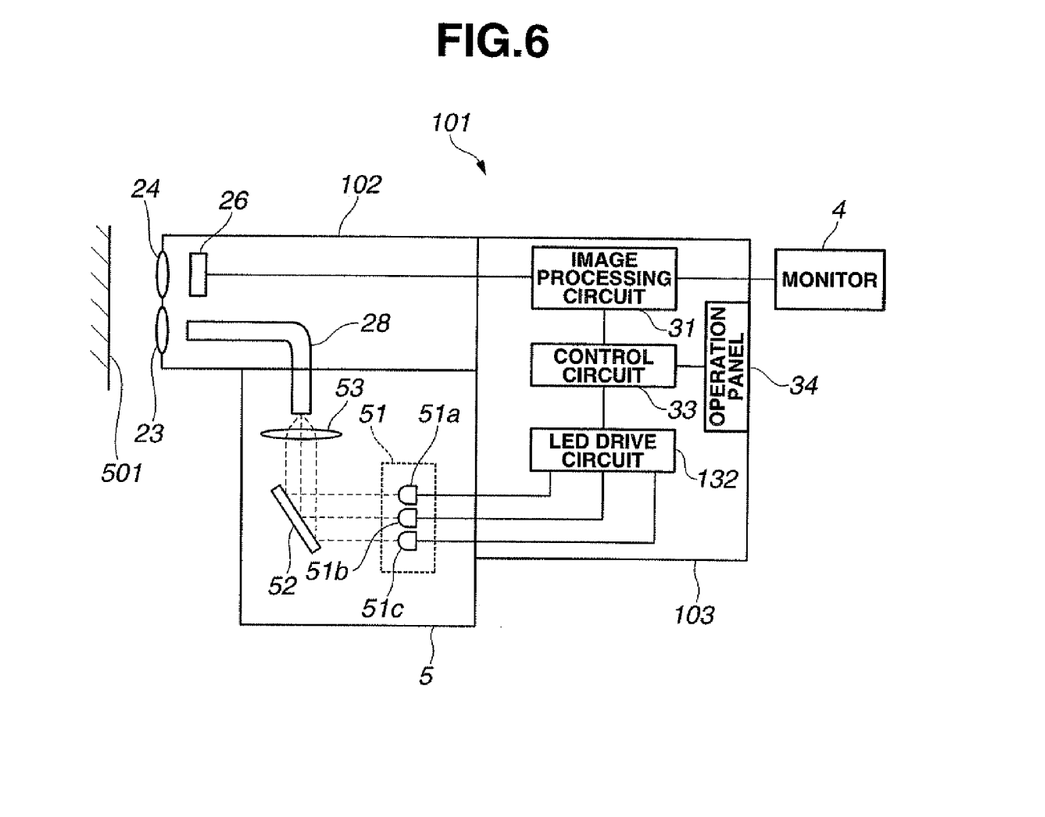
FIG. 6 is a view showing an exemplary configuration of a main part of a living body observing apparatus according to a second embodiment.
Figure 7:
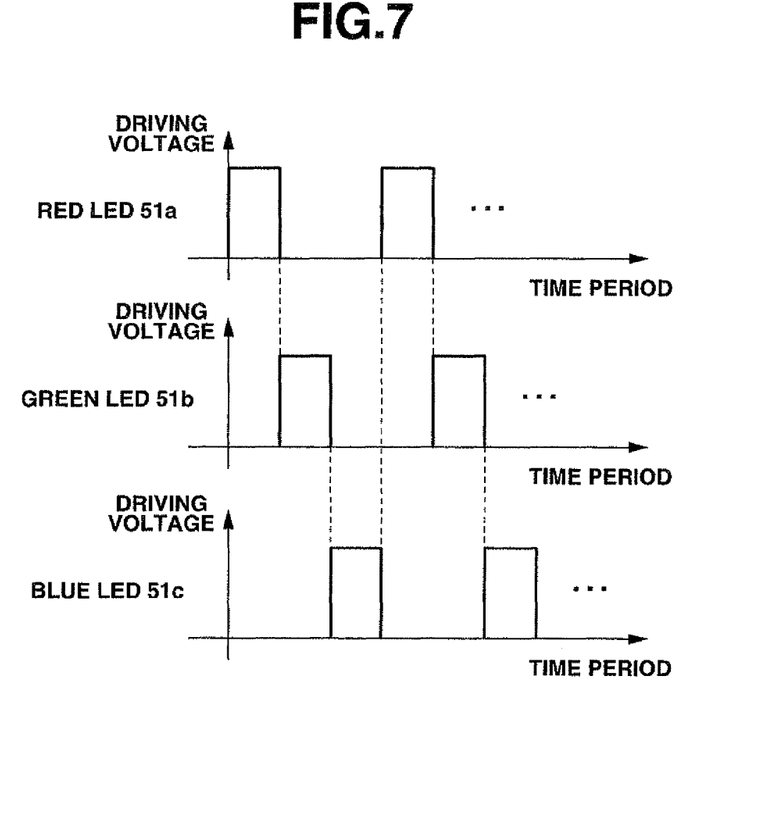
FIG. 7 is a view showing an exemplary driving voltage supplied by an image processing device according to the second embodiment to each LED in an LED group provided in a light source device.
Figure 8:
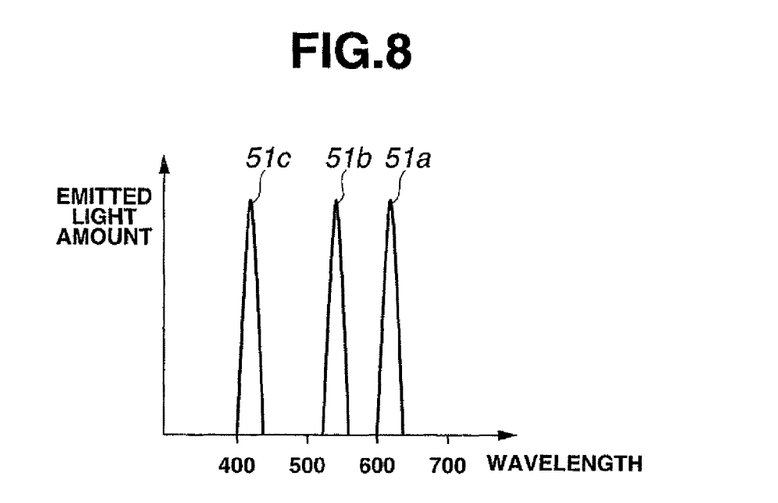
FIG. 8 is a view showing an exemplary correlation between wavelength band and emitted light amount of each of illumination lights emitted to a subject from each of the LEDs in the LED group provided in the light source device according to the second embodiment.

FIGS. 6 to 8 relate to a second embodiment of the present invention. FIG. 6 is a view showing an exemplary configuration of a main part of a living body observing apparatus according to the present embodiment. FIG. 7 is a view showing an exemplary driving voltage supplied by an image processing device according to the present embodiment to each LED in an LED group provided in a light source device. FIG. 8 is a view showing an exemplary correlation between wavelength band and emitted light amount of each of illumination lights emitted to a subject from each of the LEDs in the LED group provided in the light source device according to the present embodiment. Note that detailed description of the devices having the same configurations as those in the first embodiment is omitted. In addition, the same components as those in the first embodiment are attached with the same reference numerals, and description thereof will be omitted.

As shown in FIG. 6, a living body observing apparatus 101 includes, as a main part: a living body image pickup device 102 which is an endoscope, for example, for picking up an image of a subject 501 such as living tissue and the like in a living body as a subject to be inspected, to output the picked-up image as an image pickup signal; an image processing device 103 for generating a video signal based on the image pickup signal outputted from the living body image pickup device 102 to output the generated video signal; the monitor 4 having generally the same configuration as that in the first embodiment; and a light source device 5 for supplying illumination light to illuminate the subject 501 to the living body image pickup device 102.

The living body image pickup device 102 includes the illumination optical system 23 having generally the same configuration as that in the first embodiment, the objective optical system 24 having generally the same configuration as that in the first embodiment, the CCD (charge coupled device) 26 having generally the same configuration as that in the first embodiment, and a light guide 28 provided so as to be inserted through inside of the living body image pickup device 102.

The light guide 28 composed of an optical fiber and the like includes one end having a light incident surface arranged on the light source device 5 side, and the other end having a light emitting surface arranged on a light incident side of the illumination optical system 23. With the above-described configuration of the light guide 28, the illumination light supplied from the light source device 5 is transmitted by the light guide 28 to be emitted to the subject 501 via the illumination optical system 23.

The image processing device 103 as image processing means in the living body observing apparatus 101 includes the image processing circuit 31 having generally the same configuration as that in the first embodiment, an LED drive circuit 132, the control circuit 33 having generally the same configuration as that in the first embodiment, and the operation panel 34 having generally the same configuration as that in the first embodiment.

Based on the control signal outputted from the control circuit 33, the LED drive circuit 132 sequentially supplies for a predetermined time period a driving voltage to a red LED 51a, a green LED 51b, and a blue LED 51c, to be described later, which are provided in the light source device 5, to turn on each of the LEDs, as shown in FIG. 7, for example.

The light source device 5 includes: an LED group 51 composed of the red LED 51a, the green LED 51b, and the blue LED 51c, as illumination means in the living body observing apparatus 101; a mirror 52 for reflecting light emitted from the LED group 51; and a light condensing optical system 53 for condensing light reflected from the mirror 52 to make the light incident onto the light incident surface of the light guide 28.

The red LED 51a, the green LED 51b, and the blue LED 51c included in the LED group 51 as color separation means in the living body observing apparatus 101 respectively emit lights including wavelength bands shown in FIG. 8, for example, based on the driving voltage supplied from the LED drive circuit 132. Specifically, the red LED 51a emits light including the wavelength band of 600 nm to 630 mn, the green LED 51b emits light including the wavelength band of 530 nm to 560 nm, and the blue LED 51c emits light including the wavelength band of 400 nm to 430 nm. When the driving voltage is sequentially supplied for a predetermined time period to each of the LEDs included in the LED group 51 itself, as shown in FIG. 7 for example, the LED group 51 emits frame-sequential and narrow-band light as the illumination light for illuminating the subject 501.

Next, description will be made on working of the living body observing apparatus 101 according to the present invention.

An operator or the like turns on a power source of each of the devices of the living body observing apparatus 101, that is, the living body image pickup device 102, the image processing device 103, the monitor 4, and the light source device 5 to bring each of the devices into an activation state. Note that in the above-described activation state, it is assumed that the living body image pickup device 102 and the image processing device 103 are set in a normal observation mode.

After that, the operator or the like operates and moves the living body image pickup device 102 such that a desired subject in a living body is in a position within a field of view of the objective optical system 24, which is illuminated by frame-sequential and narrow-band light emitted from the light source device 5 via the light guide 28 and the illumination optical system 23.

The image of the subject 501 illuminated by the frame-sequential and narrow-band light emitted from the light source device 5 via the light guide 28 and the illumination optical system 23 in the state as described above is formed by the objective optical system 24 to be picked up by the CCD 26, and thereafter outputted to the image processing circuit 31 of the image processing device 3 as an image pickup signal.

The image pickup signal outputted from the CCD 26 to the image processing circuit 31 is subjected to processings such as amplification, A/D conversion, and correlated double sampling in the pre-process circuit 311 as generally the same processings as those described in the description of the first embodiment, and then, via the selector 312, subjected to the synchronization in the synchronizing circuit 313 to be inputted to the post-process circuit 314.

The post-process circuit 314 performs, based on the control signal outputted from the control circuit 33, processings such as color conversion, γ correction, and D/A conversion in the normal observation mode on the image pickup signal outputted from the synchronizing circuit 313 as generally the same processings as those described in the description of the first embodiment, and then outputs the image pickup signal subjected to the processings to the monitor 4 as a video signal.

As a result that the above-described controls and processings are performed in the living body image pickup device 102 and the image processing device 103, on the monitor 4 is displayed the image generally the same as one in a case where the desired subject in the living body is observed with the naked eye, as a subject image in the normal observation mode based on the video signal outputted from the image processing device 103.

When an instruction is given to change over the observation mode in the living body image pickup device 102 and the image processing device 103, for example, from the normal observation mode to the narrow band observation mode by an operation of the observation mode changeover switch provided on the operation panel 34 by an operator or the like, the observation mode changeover signal based on the instruction to the control circuit 33 is outputted through the operation panel 34.

The control circuit 33 outputs, based on the observation mode changeover signal outputted from the operation panel 34, control signals to the selector 312 and the post-process circuit 314 in the image processing circuit 31, and the LED drive circuit 132 to cause the selector 312, the post-process circuit 314, and the LED drive circuit 132 to respectively perform processings according to the observation mode.

Based on the control signal outputted from the control circuit 33, the selector 312 in the image processing circuit 31 outputs to one of the memories 313a, 313b, and 313c included in the synchronizing circuit 313 an image pickup signal (hereinafter abbreviated as G signal), which is outputted from the pre-process circuit 311, based on the image of the subject 501 picked up by the CCD 26 when the subject 501 is illuminated by the light emitted from the green LED 51b. Furthermore, based on the control signal outputted from the control circuit 33, the selector 312 in the image processing circuit 31 outputs to the two memories other than the above-described one memory out of the memories 313a, 313b, and 313c included in the synchronizing circuit 313 an image pickup signal (hereinafter abbreviated as B signal), which is outputted from the pre-process circuit 311, based on the image of the subject 501 picked up by the CCD 26 when the subject 501 is illuminated by the light emitted from the blue LED 51c. Note that, it is assumed that, in the narrow band observation mode according to the present embodiment, the image pickup signal, which is outputted from the pre-process circuit 311, based on the image of the subject 501 picked up by the CCD 26 when the subject 501 is illuminated by the light emitted from the red LED 51a, is cut off by the selector 312 and is not used in the subsequent processings.

Then, the image pickup signal having the two B signals and one G signal which is outputted from the selector 312 as a result of the above-described processings is subjected to synchronization in the synchronizing circuit 313, and thereafter inputted to the post-process circuit 314.

The post-process circuit 314 performs, based on the control signal outputted from the control circuit 33, processings such as color conversion, γ correction, and D/A conversion in the narrow band observation mode on the image pickup signal outputted from the synchronizing circuit 313 so as to achieve color reproduction of the blood vessels, the minute structure and the like of the mucosa surface layer of the subject in the living body with high contrast, for example, and thereafter outputs the image pickup signal subjected to the processings to the monitor 4 as a video signal.

More particularly, the post-process circuit 314 performs, as the above-described color conversion processing in the narrow band observation mode, for example, processings so as to multiply one of the two B signals in the image pickup signal outputted from the synchronizing circuit 313 by a weighting factor k1, the other of the two 13 signals by a weighting factor k2, and the G signal by a weighting factor k3. After performing the color conversion processing of the above-described content, the post-process circuit 314 further performs, based on a B channel signal composed of B signal multiplied by the weighting factor k1, a G channel signal composed of B signal multiplied by the weighting factor k2, and an R channel signal composed of G signal multiplied by the weighting factor k3, processings such as y correction and D/A conversion on the signal obtained by composing each of the channel signals to generate a video signal, and thereafter outputs the generated video signal to the monitor 4.

Note that it is assumed that the weighting factors k1, k2, and k3 used in the color conversion processing of the above-described content are real numbers. The weighting factors k1, k2, and k3, for example, may be respectively set to desired values by an operator or the like by operation of the operation panel 34, or may be fixed values set in advance in the post-process circuit 314. Furthermore, the weighting factors k1, k2, and k3 may be respectively different values, or any two of the factors or all the factors may be the same.

As a result that the above-described controls and processings are performed in the living body image pickup device 102 and the image processing device 103, on the monitor 4 is displayed an image in which the colors of the blood vessels, the minute structure and the like of the mucosa surface layer of the subject in the living body are reproduced with high contrast, as a subject image in the narrow band observation mode based on the video signal outputted from the image processing device 103.

As described above, the living body observing apparatus 101 of the present embodiment is capable of adjusting the color of the subject image in the two kinds of observation modes, that is, the not mal observation mode and the narrow band observation mode, depending on each of the observation modes, similarly as the living body observing apparatus 1 of the first embodiment. Therefore, in the observation using the living body observing apparatus 101, the operator or the like can perform the narrow band observation without using a dedicated device such as another light source device, for example. As a result, the time period to be spent on the observation of the subject in a living body can be reduced compared with the observation using a conventional apparatus.

Note that it is needless to say that the present invention is not limited only to the above-mentioned embodiments, but may be modified and embodied in various forms without departing from the scope of the present invention.

This application is filed claiming priority from Japanese Patent Application No. 2005-219468 applied in Japan on Jul. 28, 2005, the disclosed contents of which being incorporated in the present specification, claims, and drawings.

The invention claimed is:

1. A living body observing apparatus comprising:
an illumination section including one or a plurality of semiconductor light emitting elements for emitting illumination light to illuminate a subject;
an image pickup section for picking up an image of the subject illuminated by lights of respective color wavelength bands emitted from the illumination section, and outputting the picked-up image as an image pickup signal separated so as to at least include two color components of a green component and a blue component; and
an image processing section for performing a predetermined processing on the image pickup signal outputted from the image pickup section, and outputting the processed image pickup signal as a video signal to display the image of the subject on a display section,
wherein, when a red component is included in the image pickup signal, the image processing section removes the red component before performing the predetermined processing, and further performs, as the predetermined processing, color conversion processing to convert the blue component in the image pickup signal into a green component in the video signal, and convert the green component in the image pickup signal into a red component in the video signal, and thereafter performs weighting processing respectively on the red component and the green component in the video signal.

2. The living body observing apparatus according to claim 1, wherein the illumination section includes a fluorescent member for emitting fluorescence as the illumination light excited by excitation light including a predetermined wavelength band and the semiconductor light emitting element emits the excitation light to the fluorescent member.

3. The living body observing apparatus according to claim 1, wherein the illumination section, and the image pickup section are provided inside of an endoscope.

4. The living body observing apparatus according to claim 1, wherein the illumination section, and the image pickup section are provided inside of an oral camera.

5. The living body observing apparatus according to claim 2, wherein the predetermined wavelength band is in blue range.

6. The living body observing apparatus according to claim 2, wherein the fluorescence is light including blue or green wavelength band.

7. The living body observing apparatus according to claim 5, wherein the fluorescence is light including blue or green wavelength band.

8. A living body observing apparatus comprising:
an illumination section including one or a plurality of semiconductor light emitting elements for emitting illumination light to illuminate a subject;
an image pickup section for picking up an image of the subject illuminated by lights of respective color wavelength bands emitted from the illumination section, and outputting the picked-up image as an image pickup signal separated so as to at least include two color components of a green component and a blue component; and
an image processing section for performing a predetermined processing on the image pickup signal outputted from the image pickup section, and outputting the processed image pickup signal as a video signal to display the image of the subject on a display section,
wherein, when a red component is included in the image pickup signal, the image processing section removes the red component before performing the predetermined processing, and further performs, as the predetermined processing, color conversion processing to convert the blue component in the image pickup signal into a green component and a blue component in the video signal, and convert the green component in the image pickup signal into a red component in the video signal, and thereafter performs weighting processing respectively on the red component, the green component, and the blue component in the video signal.

9. The living body observing apparatus according to claim 8, wherein the illumination section includes a fluorescent member for emitting fluorescence as the illumination light excited by excitation light including a predetermined wavelength band, and the semiconductor light emitting element emits the excitation light to the fluorescent member.

10. The living body observing apparatus according to claim 8, wherein the illumination section, and the image pickup section are provided inside of an endoscope.

11. The living body observing apparatus according to claim 8, wherein the illumination section, and the image pickup section are provided inside of an oral camera.

12. The living body observing apparatus according to claim 9, wherein the predetermined wavelength band is in blue range.

13. The living body observing apparatus according to claim 9, wherein the fluorescence is light including blue or green wavelength band.

14. The living body observing apparatus according to claim 12, wherein the fluorescence is light including blue or green wavelength band.

15. A living body observing apparatus comprising:
an illumination section including a blue semiconductor light emitting element for emitting light having a peak in a blue wavelength band to a subject, and one or a plurality of semiconductor light emitting elements for respectively emitting light having a peak in a color wavelength band different from the blue wavelength band to the subject;
an image pickup section for picking up an image of the subject illuminated by lights of respective color wavelength bands emitted from the illumination section, and outputting the picked-up image as an image pickup signal separated so as to at least include two color components of a green component and a blue component; and
an image processing section for performing a predetermined processing on the image pickup signal outputted from the image pickup means, and outputting the processed image pickup signal as a video signal to display the image of the subject on a display section,
wherein, when a red component is included in the image pickup signal, the image processing section removes the red component before performing the predetermined processing, and further performs, as the predetermined processing, color conversion processing to convert the blue component in the image pickup signal into a green component in the video signal, and convert the green component in the image pickup signal into a red component in the video signal, and thereafter performs weighting processing respectively on the red component and the green component in the video signal.

* * * * *